United States Patent [19]

Udovich et al.

[11] 4,248,998

[45] Feb. 3, 1981

[54] 2,3-DI-(CARBOXYPHENYL)OXIRANE COMPOUNDS AND POLYMERS

[75] Inventors: Carl A. Udovich, Joliet; Edward E. Paschke, Wheaton; Ellis K. Fields, River Forest, all of Ill.

[73] Assignee: Standard Oil Company (Indiana), Chicago, Ill.

[21] Appl. No.: 67,675

[22] Filed: Aug. 20, 1979

[51] Int. Cl.$^3$ .................... C08K 59/42; C07D 303/16; C07D 303/14

[52] U.S. Cl. ............................... 528/296; 260/30.4 R; 260/348.25; 260/348.62; 528/73; 528/176; 528/194; 528/297; 528/341

[58] Field of Search ...................... 260/348.25, 348.62, 260/30.4 R; 528/297, 176, 302, 296, 341, 73, 194

[56] References Cited

U.S. PATENT DOCUMENTS

| | | | |
|---|---|---|---|
| 2,999,868 | 12/1961 | Phillips et al. | 260/348.62 |
| 3,842,040 | 10/1974 | Browne | 528/176 |

OTHER PUBLICATIONS

J. Polymer Science, Poly. Chem. Ed. 14, 2669 (1976), CA 65 841f.

*Primary Examiner*—V. P. Hoke
*Attorney, Agent, or Firm*—William C. Clark; William T. McClain; William H. Magidson

[57] ABSTRACT

2,3-Di-(carboxyphenyl) oxirane compounds and essentially linear polyesters and copolyesters therefrom. The esters are useful as plasticizers for polyvinylchloride.

24 Claims, No Drawings

2,3-DI-(CARBOXYPHENYL)OXIRANE COMPOUNDS AND POLYMERS

BACKGROUND OF THE INVENTION

The field of this invention relates to aromatic polyacyl compounds of polyphenyl structure suitable for polymers useful for forming shaped objects, such as film, fiber and molded parts. The esters are suitable as plasticizers for polyvinylchloride and other polymers.

As is well known, the mechanical and physical properties of a fiber or film depend on the chemical structure of the polymer from which they are made. For example, the melting point, molding temperature, and glass transition temperature of the polymer composition control many of the physical properties and fabrication of the shaped objects. The melting point determines thermal resistance and heat-setting temperature of fibers. Molding temperature determines fabrication temperature. Glass transistion temperature (Tg) determines initial modulus, tensile strain recovery, work of recovery, drape and hand, wash-and-wear characteristics, comfort factors, and resilience of fibers. The main molecular factors that influence these properties include chain stiffness, the intermolecular forces, orientation, and crystallinity.

Accordingly, there has been considerable interest in developing aromatic symmetrical acids as precursors for thermally stable polymers, such as polyesters or polyamides. It is well known that the introduction of aromatic units in the polymer chain backbone results in high bond energies, a low degree of reactivity, and rigidity of the polymer chain structure. The use of aliphatic units in the polymer chain backbone results in flexibility, lower temperature characteristics, and decreased strength as compared with the aromatic types.

Substantially all commercial polyester fibers are based on terephthalic acid. While these fibers have many excellent properties there is a need for polyester fibers having a higher Tg than provided by terephthalic acid polyesters. Recently, 2,6-naphthalene dicarboxylic acid has been proposed as a suitable aromatic acid for producing polyesters suitable for tire cord. This acid provides polyesters having a higher Tg than those based on terephthalic acid. For example, poly(ethylene terephthalate) has a Tg of 74° C. whereas poly(ethylene 2,6-naphthalate) has a Tg of 115°-125° C. However, the difficulties of manufacturing the precursor, i.e., 2,6-dimethylnaphthalene, have made the production of this acid technically difficult and economically costly. The acid can require a four-step synthesis with attendant loss in yield and consequent high cost.

Various other organic polymers have been suggested for use as high temperature fibers, such as copolyamides (Kevlar), polybenzimidazoles, polyoxadiazoles, polyimides and phenylene ring systems (polyphenylenes). Polyarylates and polycarbonates have been suggested for use as engineering plastics. However, all of these are costly and/or difficult to manufacture. Accordingly, there is a need for new aromatic acids suitable for preparing polymers for many uses.

It is the object of this invention to provide a new group of aromatic polycarboxylic acids of polyphenyl structure that will meet this need. Another object of this invention is to provide a process for making these acids. Another object of this invention is to provide a new polycarboxylic acid, specifically 2,3-di-(4-carboxyphenyl) oxirane, for use in polymer chains. A further object is to provide novel polymers, both polyesters and copolyesters, made from these acids. Other and further objects of this invention will be apparent from the following description.

The field of this invention, accordingly, has three aspects. First, it relates to novel compositions of matter that are oxirane polyphenylacyl compounds and to the method of preparing these acyl compounds. Second, it relates to novel polyesters based on oxirane polyphenylacyl compounds. Third, it relates to novel copolyesters based on these same novel acyl compounds.

These novel oxirane polyphenylacyl compounds (acids, acyl halides, simple esters, e.g., methyl, etc.) are desirable intermediates for producing condensation polymers, such as polyesters and copolyesters suitable for shaped articles as film, fiber, and molded parts. The esters of these acids and monohydric alcohols containing 1 to 24 carbon atoms can be used as plasticizers for polyvinylchloride (PVC).

It has been found in accordance with this invention that 2,3-di-(4-carboxyphenyl) oxirane can be prepared by the peracid epoxidation of stilbenedicarboxylic acid and polymers therefrom with diols and other dibasic acids to produce polyesters and copolyesters in which the epoxide moiety is retained. Cross-linking of the polyester or copolyester initiated by strong acids or bases affords a finished polyester or copolyester with improved properties, such as tensile strength, melting point, and solvent resistance. The finished polyesters and copolyesters are suitable for use in coatings, as a polymeric stabilizer and/or as polymers suitable for forming shaped objects such as film, fiber and molded parts.

Accordingly, this invention relates to a new family of compositions of matter having the structural formula

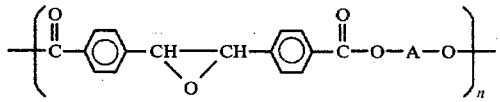

wherein A is selected from the group consisting of divalent aliphatic or alkylene moieties and divalent aromatic moieties consisting of an alkylene group, a cycloakylene group and an alkylene-oxyalkylene group containing from two to 24 carbon atoms and an arylene group containing a benzenoid ring radical selected from the group consisting of phenylene, naphthylene, anthrylene, phenanthrylene, benzothienylidene, and fluorenylidene moieties and ring substitution products thereof, and n is an integer from 1 to 8,000. More particularly, it relates to compositions of matter wherein a condensation polymer of a diol HO—A—OH and an epoxide of stilbene dicarboxylic acid or derivative thereof, are reacted with formation of a polyester retaining the epoxy unit, and wherein the diol is an alkanediol and A is ethylene, propylene, trimethylene, 1,3-isobutylene, pentamethylene, neopentylene, 2,2-diethyl-1,3 propylene, hexamethylene, 2,2,4-trimethyl-1,3-pentylene, 2-methyl-2,4-pentylene, decamethylene, 1,4-cyclohexylene, 1,4-cyclohexanedimethylene and ethyleneoxyethylene. The alkanediols can be obtained from a variety of commercially available alkanediols. Examples of such compounds include ethylene glycol, propylene glycol, 1,4-butylene glycol, 2,2-dimethyl 1,3-propanediol, 2-methyl-3-ethyl-1,3-propanediol, 2,2- diethyl-1,3-propanediol, 1,6-hexanediol, 1,10-decanediol, diethylene glycol, 1,4-cyclohexanediol, etc.

This invention also relates to a new family of resins which are essentially linear copolyesters comprising units of a polyhydric alcohol component comprising at least one dihydric alcohol moiety and a dicarboxylic component wherein said dicarboxylic component comprises terephthalate moieties and 2,3-dicarboxyphenyl oxirane moieties in a range of mole ratios of from 19:1 to 1:19.

Syntheses of epoxides and of trans-stilbene oxide (*Organic Syntheses*, 4, 860, Wiley, N.Y. (1963)) are well-known in the prior art. trans-Stilbene oxide has been prepared by the reaction of silver oxide with the methiodide of 1,2-diphenyl-2-dimethylaminoethanol, by the reaction of hydrazine with hydrobenzoin, and the reaction of peracetic acid or perbenzoic acid with trans-stilbene. However, to the best of our knowledge, epoxides of stilbenedicarboxylic acid are heretofore unknown. Moreover, although it is known in the prior art that compounds containing the epoxide group such as the oxetane ring and oxirane ring are easily polymerized and undergo further reaction by means of the oxetane ring and oxirane ring, epoxides of stilbenedicarboxylic acid and polymers therefrom which retain the oxirane ring, to the best of our knowledge, are heretofore unknown. And although polymeric derivatives of 3,3-bis(aminomethyl)-oxetane and of epoxysuccinyl chloride are in the prior art (T. W. Campbell and R. N. McDonald, *J. Polymer Sci.*, A-1, 1, 2525 (1963) and syntheses of polyesters by epoxidation of unsaturated polyesters have been taught (*J. Poly. Sci.*, Poly. Chem. Ed., 14, 2969 (1976)) it is clear, to the best of our knowledge, that essentially linear polyesters containing the oxirane ring conjointly with two benzene rings have not been known.

In the prior art, the synthesis of polymers with monomers containing the oxetane ring resulted in polymers which showed a strong tendency to crosslink, either on standing at room temperature or on heating at 100°–120° C. overnight or for 24 hours. (T. W. Campbell, et al., *J. Poly. Sci.*, op. cit. p. 2528). Polymers were difficult to obtain uncrosslinked, presumably because of cleavage of the oxetane ring. Synthesis of polyamides having epoxy groups has been reported (*J. Appl. Poly. Sci.*, 23, 827–835 (1979)) wherein dicarboxylic acid chloride having an epoxy group has been used as a monomer. Low temperature and interfacial polycondensations of dicarboxylic acid chloride having an epoxy group with aromatic diamines have been carried out to obtain polyamides having epoxy groups. However, ring opening reactions of epoxy groups using excess amines gave products having poor thermal stability, that is, their decomposition temperatures were lower than those of the original polymers having epoxy groups.

Accordingly, while it is known in the prior art to prepare polyamide polymers containing the oxetane ring or the oxirane ring, the polyamide polymers prepared heretofore have demonstrated characteristics of instability upon standing or heating and the opening of the oxetane ring or the oxirane ring. The reactivity of oxirane ring toward alcohols, amines, diols and diamines as well as to the influence of heat renders the stability of the instant invented family of compounds unexpected and surprising.

It is also well known that stilbenedicarboxylic acid is a versatile chemical building block. U.S. Pat. No. 2,657,195 teaches the preparation of linear polymers from stilbene dicarboxylic acid. The resulting polymer can have recurring units containing double bonds that can be used to alter the character of the molecule after polymer formation by reaction with compounds capable of adding to a double bond. U.S. Pat. No. 3,496,839 teaches preparation of linear unsaturated polyesters produced from 4,4'-stilbenedicarboxylic acid and commercially available alkanediols wherein a process of irradiation improves the physical properties of the polymer with improved heat stability, solvent resistance and tensile strength. U.S. Pat. No. 2,657,194 teaches a process for forming polymers with improved dye receptivity by reaction of a stilbenedicarboxylic acid by using as catalyst Na and Mg with a polyoxyalkylene glycol. U.S. Pat. No. 2,895,947 teaches preparation of esters by the reaction of epoxy-substituted alcohols such as 2,3-epoxypropanol with p,p'-stilbenedicarboxylic acid using tertiary amines as catalysts. U.S. Pat. No. 2,997,391 teaches the preparation of light-sensitive polyamides containing stilbenes by reacting a stilbene with a diamine, a dibasic acid or ester, or amino acid or ester. Swiss Pat. No. 506,583 (C.A. 75, 141977i) teaches stilbenyloxadiazoles, useful as fluorescent whiteners in poly(ethylene terephthalate), nylon 66, and polypropylene. 4-Benzoxazolyl-4'-oxadiazolylstilbenes are prepared by condensing an oxadiazolylstilbenecarboxylic acid with an orthoaminophenol (C.A., 66, 116,706b). Preparation of bis(2-benzoxazolyl) stilbene derivatives for use as optical brightening agents has been taught (Neth. Appl. 6,413,267; C.A., 64, 6800d). 4,4'-Disubstituted stilbenes are prepared by treating stilbene -4,4'-dicarboxylic acid dichlorides with monocarboxylic acid hydrazides (C.A., 65, 841f).

Accordingly, while it is well known to prepare polymers containing the oxetane ring or the oxirane ring, and stilbene derivatives containing stilbenes, the preparation of a stilbene acyl derivative containing an epoxy group has not been known and, notably, the preparation of a stable polymer containing the epoxide group and the stilbene moiety has not been known.

SUMMARY OF THE INVENTION 2,3-Di-(carboxyphenyl) oxirane and essentially linear polyesters, copolyesters therefrom. The simple esters are useful as plasticizers for polyvinylchloride.

DETAILED DESCRIPTION OF THE INVENTION

The compositions of this invention relate to diacyl compositions and condensation polymers of 2,3-di-(carboxyphenyl) oxirane, such as 2,3-di-(4-carboxyphenyl) oxirane (DCO), prepared by the peracid epoxidation of 4,4'-stilbenedicarboxylic acid. The 2,3-di-(4-carboxyphenyl) oxirane undergoes condensation polymerization with diols alone and in admixture with other dibasic acids and diols to produce polyesters and copolyesters in which the epoxide unit is retained. These condensation polyesters display high glass transition temperatures and possess a functional unit, the epoxide, which can be utilized for polymer crosslinking to improve physical properties such as tensile strength, melting point, and solvent resistance. The invention is illustrated by the following equations:

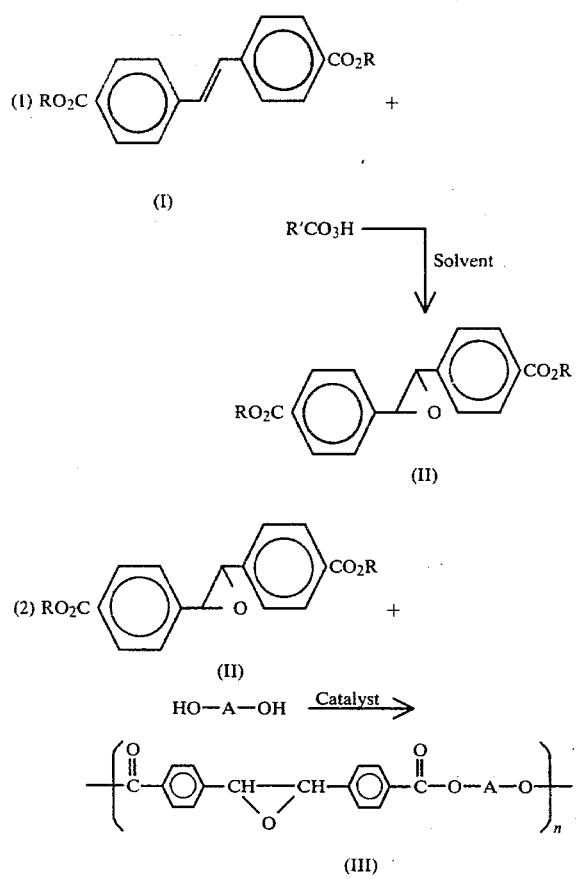

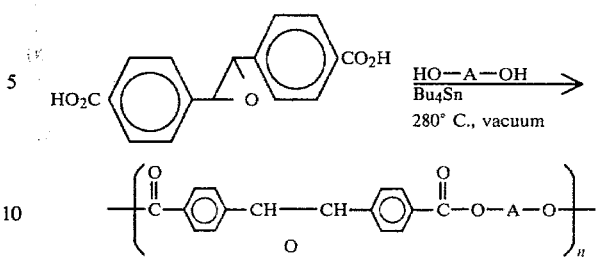

The diol is such that A may be aliphatic or aromatic such as alpha, omega-alkanediols, di-phenols, etc. Typical condensation polymerization catalysts such as tetrabutyltin can be used.

We project this flow diagram for the production of DCO esters from p-xylene and subsequent polyester formation.

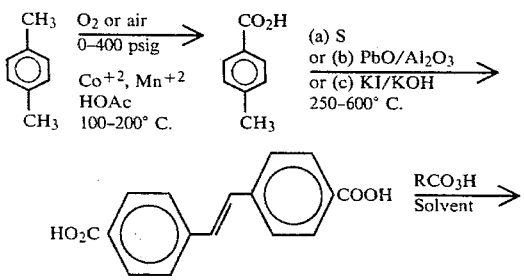

In equation (1), R groups are usually the same and may be hydrogen, alkyl, aryl or alkaryl. The R' group of the peracid, R'CO₃H, may be alkyl, aryl or alkaryl. The solvent is typical for epoxidation reactions and includes chlorinated hydrocarbons. In equation (2), condensation poymerization with a diol HO-A-OH is indicated with formation of a polyester (III) retaining the epoxy unit, Oxidation of p-xylene to p-toluic acid is followed by dehydrodimerization by (a) sulfur, or (b) PbO on alumina, or (c) KOH/KI to the 4,4'-stilbenedicarboxylic acid, which is epoxidized and then polymerized with the diol of choice with or without a co-acid with typical catalysts and conditions.

The procedure most generally used for the preparation of epoxides can be used which comprises the peroxy acid oxidation of a suitable olefin. Among the peroxy acids that can be used for the conversion of olefins into epoxides are peroxyformic, peroxyacetic, peroxybenzoic, monoperoxyphthalic, and trifluoroperoxyacetic. Peroxyformic and peroxyacetic acids require a buffered medium to prevent rupture of the oxide ring by excess acid.

Esters of 2,3-di-(4-carboxyphenyl) oxirane and the esters of the other acids can be produced by reacting the appropriate dicarboxylic acid compound (free acid or acyl halide) with a suitable monohydroxy compound at a temperature of 60° to 200° C. or the dimethyl ester can be produced first and the appropriate diester produced by transesterification with a suitable monohydroxy compound at a temperature of 60° to 200° C.

The esters of polyphenyl carboxylic acids of this invention are useful as plasticizers of polyvinylchloride and other polymer formulations. Suitable monohydric alcohols useful for producing the ester include aromatic or aliphatic, straight or branched chain, substituted or unsubstituted compounds of from 1 to 24 carbon atoms. Examples are alcohols such as methyl alcohol, ethyl alcohol, propyl alcohol, butyl alcohol, cyclohexyl alcohol, heptyl alcohol, dodecyl alcohol, ocytl alcohol, isotridecyl alcohol, stearyl alcohol, oleyl alcohol, tetracosyl alcohol, as well as aromatic hydroxy compounds containing from 6 to 24 carbon atoms such as phenol, naphthol, cresol, parastearylphenol, etc.

These esters can be produced under conventional reaction conditions by reacting from about 1 to 10 moles of monohydroxy compound per carboxyl equivalent of said acid compound to form a solution of ester and monohydroxy compound. If desired esterification catalysts or transesterification catalysts can be used, such as sulfuric acid, phosphoric acid, para-toluene sulfonic acid, benzene sulfonic acid, stannous octoate, boron trifluoride etherate, tetraalkyl titanates, and zirconates of U.S. Pat. No. 3,056,818 etc.

The esters of monohydroxy compounds containing from 1 to 4 carbon atoms in each alkyl group can be used advantageously in ester interchange processes for producing high molecular weight polyesters while the esters containing from 1 to 24 carbon atoms in each ester moiety, preferably alkyl groups containing from about 4 to 13 carbon atoms, can be used as plasticizers for resinous polymers of vinyl chloride containing at least 50 mole percent vinyl chloride units. The resinous polymers of vinyl chloride include homopolymeric polyvinyl chloride, 95/5 vinyl chloride/vinyl acetate copolymers, etc. The plasticizers can be used in a concentration of from 5 to 300 parts by weight per each 100 parts by weight resinous polymer of vinyl chloride as the sole plasticizer or together with other plasticizers such as dioctyl phthalate, trioctyl phosphate, epoxidized glyceride oils, etc.

The polyphenyl dicarboxylic acids can be used to produce high molecular weight essentially linear condensation polymers, such as polyesters. These can be made by condensing at least one of the novel diacyl compounds with an organic compound providing at least two reactive groups derived from a polyhydric alcohol. These polyols can be saturated or unsaturated aromatic or aliphatic, straight or branched chain, substituted or unsubstituted.

The polyphenyl dicarboxylic acids can be used to produce high molecular weight essentially linear polyamides. These can be made by condensing at least one of the novel diacyl compounds with a polyamine, a polyisocyanate or a polyisothiocyanate. However, the oxirane ring may not be stable upon standing or heating with consequent opening of the oxirane ring.

Broadly speaking, the polyesters of this invention can be made by reacting polyhydric alcohol with the appropriate polycarboxylic acid or lower alkyl (preferably methyl) ester of the polycarboxylic acid. In those cases where the polyester is composed of essentially one dihydric alcohol (ethylene glycol or butylene glycol) and the two essential dicarboxylic acid monomers (terephthalic acid and 2,3-di-(4-carboxyphenyl) oxirane these polyesters can be produced by reacting dihydric alcohol with one or more of the acids or their ester-forming derivatives. Alternatively, one of the acid monomers can be reacted with dihydric alcohol and then the second acid monomer condensed. The dihydric alcohol component can comprise a plurality of dihydric alcohols, two or more being selected from the group consisting of ethylene glycol, propylene glycol, etc.

The polyhydric alcohol dicarboxylate copolyester can be prepared directly from a plurality of dicarboxylic acids, or an ester-forming derivative of the dicarboxylic acid or acids may be used, i.e., an acid halide, its anhydride, and/or an ester thereof, particularly an ester of the dicarboxylic acid with a lower aliphatic alcohol or with phenol. Correspondingly, a plurality of ester-forming derivatives of polydric alcohols can be employed, i.e., a derivative of the alcohol containing functional groups equivalent to the hydroxyl groups in their ability to react with carboxyl groups. Thus, an alcohol can be employed in the form of an epoxide, and/or ester of the alcohol with acetic acid or other lower aliphatic acid may be used.

A convenient method for preparing the polyesters of this invention comprises reacting the acid or dimethyl ester of the dicarboxylic acid with an excess of the polyhydric alcohol, approximately 1.1 to 2.5 moles of alcohol per mole of ester, preferably about 1.5 to 2.1 moles of alcohol per mole of ester. For example, ester interchange reaction can be carried out at atmospheric pressure but higher or lower pressure may be used if desired. A range is usually from 0.1 to 10 atmospheres. Temperature range is usually from 90° C. to 325° C. Following the ester interchange reaction in which methanol is removed as a by-product, heating is continued at an increased temperature to bring about polycondensation. Small amounts of catalysts usually are added to facilitate the reaction, manganous acetate, calcium acetate, and sodium methoxide being typical ester interchange catalysts, and antimony trioxide, dibutyltin maleate, and zinc acetate being suitable polycondensation catalysts. Litharge, sodium hydrogen hexabutoxytitanate and the tetra-alkyl titanates, such as tetra-isopropyl titanate, are examples of catalysts that can be used for both the ester interchange and the polycondensation steps. Normally, the polycondensation reaction is continued until a degree of polymerization is achieved corresponding to an inherent viscosity of approximately at least 0.20 dl/g in a 60/40 phenol-tetrachloroethane solvent at 30° C.

To achieve a higher degree of polymerization, the product of the polycondensation reaction is allowed to cool to room temperature, about 20° to 25° C., forming a solid material. The solid is ground to flake, following which the flake is heated below its melting point in a stream of inert gas to achieve solid phase polycondensation.

For purposes of this invention, the term "alkylene" is defined as including divalent groups having 2 to 20 carbon atoms in the alkylene chain. For purposes of this invention, the term "aromatic moiety" is defined as including divalent aromatic radicals characterized by at least one benzene ring, i.e., the six-carbon ring of benzene or the condensed six-carbon rings of the other aromatic radicals such as naphthylene, phenanthrylene, anthrylene, etc. The term "aromatic moiety" is further defined as including radicals containing two benzene rings joined by a divalent group such as a methylene group, ether, sulfone, sulfide groups, etc. Examples of these radicals are phenylene, biphenylene, diphenylene ether, diphenylenemethane, diphenylene sulfone, and diphenylenesulfide. One or more hydrogens of the aromatic nucleus can be replaced by nonreactive radical groups such as lower alkyls, halogens and nitro radicals.

The polyesters of this invention comprise a polyhydroxy component comprising one or more polyhydric alcohols (diols, triols, etc.) and a polycarboxylic acid component comprising one of the polyphenyl dicarboxylate components. The preferred polyesters of this invention are essentially linear and comprise units of alkylene glycols containing 2 to 10 carbon atoms and polyphenyl dicarboxylate moieties. The polyesters based on 2,3-di-(4-carboxyphenyl) oxirane have an exceptionally high Tg. For example, homopolymeric polyethylene-2,2',6,6'-tetramethylbiphenyl-4,4'-dicarboxylate has a Tg of about 191° C. Molding temperature is about 240° C. Homopolymeric tetramethylene-2,2',6,6'-tetramethylene-4,4'-dicarboxylate has a Tg of 131° C. Homopolymeric polyethylene terephthalate has a Tg of about 70°–75° C. and a molding temperature of 260°–270° C. Homopolymeric polyethylene naphthalene 2,6-dicarboxylate has a Tg of 115°–125° C.

The glass transition temperature (Tg) of polyesters of 2,3-di-(4-carboxyphenyl) oxirane and diols of chain lengths of up to six carbon atoms (DCO polyesters) as well as that of polyethylene terephthalate and other polyesters for comparison are given in the following table.

TABLE I

Thermal Properties of DCO Polyesters and Other Polyesters

| Diacid | Diol | Tg °C. |
|---|---|---|
| 2,3-Di-(4-carboxy-phenyl) Oxirane (DCO) | Ethylene Glycol | 203 (calculated) |
| | 1,4-Butanediol | 137 (calculated) |
| | 1,6-Hexanediol | 116 |

TABLE I-continued

| Thermal Properties of DCO Polyesters and Other Polyesters | | |
| --- | --- | --- |
| Diacid | Diol | Tg °C. |
| Terephthalic | Ethylene Glycol | 70 |
| | 1,4-Butanediol | 22 |
| 2,6-Naphthalene | Ethylene Glycol | 115–125 |

Since wash and wear characteristics of textile produced from polyester fiber are a function of the Tg of the fiber, it is desirable to employ fibers having a Tg above 100° C. For example, the Tg of the polyester of DCO and ethylene glycol is well over 200° C. Accordingly, the polyesters of this invention have a singular advantages over PET, i.e., 203° C. for the ethylene DCO polyester versus about 74° C., in wash and wear clothing.

Polyesters based on terephthalic acid, particularly polyethylene terephthalate, have been used for the manufacture of fibers and films because of the many desirable properties of the polymer, such as high mechanical strength, low water absorption and resistance to many chemicals. Recently, there has been considerable interest in the use of polybutylene terephthalates in fiberglass molding compositions. In addition to the foregoing, there are indications that polyethylene terephthalate may be used in large volumes for the production of containers, particularly those suitable for packaging carbonated beverages and various other food products. For this used, the polyethylene terephthalate has the advantage of relatively low permeability to carbon dioxide, low water absorption and low permeability to various other products indigenous to foods.

As pointed out in U.S. Pat. No. 3,535,286, polyethylene terephthalate crystallizes too rapidly for some uses. While the undesirably high crystallization tendency can be reduced by replacing part of the terephthalic acid or the polyhydric alcohol, most of the potential replacement compounds do not substantially improve the undesirable properties of the polymer. Further, such compounds generally reduce the glass transition temperature of the polyalkylene terephthalates and reduce the utility of the polymer. Polyethylene terephthalate (PET) has a relatively high molding temperature of approximately 260°–270° C. and a Tg (glass transition temperature or second order transition temperature) of about 75° C. The relatively low glass transition temperature of the polyester can lead to fusion of polyethylene terephthalate fibers in fabrics during home dryer use or ironing.

The relatively large gradient between the molding temperature of the polymer and the second order transition temperature of the polymer creates several problems in PET molding applications. For example, in the production of polyester bottles, polyethylene terephthalate must be molded at a temperature of about 275° C. and then cooled down to about the second order transition temperature prior to orientation to form an oriented (biaxially or monoaxially oriented) bottle. It is generally recognized that the cooling period is the time limiting step in the production of oriented polyethylene terephthalate bottles. Accordingly, there is a need for co-monomers which are capable of lowering the molding temperature of polyethylene terephthalate without adversely affecting the second order transition temperature of the PET polymer.

Although the crystals of a polymer melt over a temperature range, there is a temperature above which the crystals cannot exist. This temperature is defined as the melting point. Molding temperature or fabrication temperature is defined as the temperature at which the polymer has sufficient flow to be converted to a shaped article. Typically, the molding temperature is higher than the melting point temperature. The second order transition temperature (or Tg) represents the temperature at which the polymer passes from the glassy form into the elastic form and vice versa. In the case of copolymerization, the molding temperature and Tg temperature generally decrease, and, in the cases where increases are demonstrated, such increases are generally small. Surprisingly, the inclusion of the 2,3-di-(4-carboxyphenyl) oxirane as a co-monomer in terephthalic acid polyester lowers the molding temperature and increases the Tg. The increased ease in processing PET as well as the economic advantage of lower melt temperatures, i.e., requiring less heat input to reach melt temperature, incrases the economic utility of PET.

Another object of this invention accordingly is to provide new terephthalate polyesters having a relatively low molding temperature without reduction of the second order transition temperature of the polymer. Another object of this invention is to provide polyalkyleneterephthalate polyesters having improved physical properties. Other objects appear hereinafter.

We have now found that essentially linear copolyesters comprising units of dihydric alcohol and a dicarboxylate component wherein said dicarboxylate component comprises terephthalate moieties and 2,3-di-(carboxyphenyl) oxirane moieties have a higher second order transition temperature than the homopolymeric polyester. The polyesters of this invention can have a terephthalate to 2,3-di-(carboxyphenyl) oxirane mole ratio range of from approximately 19:1 to 1:19. In general, as the concentration of 2,3-di-(carobxyphenyl) oxirane moieties increase in the polymer, the Tg of the polymer increases.

While it is generally preferred that the two essential acyl monomers (terephthalic acid and 2,3-di-(carboxyphenyl) oxirane) comprise from 95–100% of the acyl equivalents in the polyesters of this invention, these co-monomers can comprise as little as 75% of the acyl equivalents. Other suitable acid co-monomers include aromatic polycarboxylic acids, such as phthalic acid, phthalic anhydride, isophthalic acid, 2,6-naphthalene dicarboxylic acid, trimellitic anhydride, trimellitic acid, etc.; saturated aliphatic polycarboxylic acids, such as adipic acid, sebacic acid, 1, 2, 3, 4-butane-tetracarboxylic acid, etc.; unsaturated aliphatic dicarboxylic acids, such as maleic acid, maleic anhydride, fumaric acid, etc. In general, the organic acids or acyl compounds containing three or more acyl groups can comprise up to about 2% of the acyl equivalents in the polyester and the difunctional organic acids comprise at least 98%.

In those cases where an alpha, beta-ethylenically unsaturated acid compound (maleic anhydride, fumaric acid, etc.) is used, the resulting polyester can be dissolved in a monovinyl aromatic (styrene, vinyltoluene, etc.) and can be used in molding compositions in the same manner as other unsaturated polyesters.

The polyhydric alcohols useful in the copolyesters of this invention include alkylene glycols containing from about 2–12 carbon atoms, such as ethylene glycol, 1,3-propylene glycol, 1,2-propylene glycol, 1,4-butylene glycol, hexamethylene glycol, dodecamethylene glycol, etc.; aromatic polyhydric alcohols, such as hydroquinone, resorcinol, Bisphenol A, etc.; cycloaliphatic glycols such as 1,4-dimethylol cyclohexane, dimethylol cyclobutane, etc.; polyoxyalkylene glycols, such as polyoxyethylene glycols, polyoxypropylene glycols, block copolymers of polyethylene and polypropylene glycol, polytetramethylene glycols, etc; neopentyl glycol, polyhydric alcohols having three or more hydroxy groups, such as 1,1,1-trimethylol ethane, 1,1,1-trimethylol propane, pentaerythritol, sorbitol, reaction products of the aforesaid polyhydric alcohols having a functionality of three or more with alkylene oxides (ethylene oxide or propylene oxide) such as those sold for use in the production of flexible polyurethane foams, etc. In general, the polyhydric alcohols having a functionality of three or more should provide no more than about 2 mole % of the polyester. For optimum properties, it is generally preferred that either ethylene glycol or butylene glycol comprise approximately 100 mole % of the polyol portion of the copolyester of this invention since, as pointed out above, the large volume polyesters of commerce are the polyethylene terephthalates and the polybutylene terephthalates.

In more detail, the stilbenedicarboxylic acids and their esters can be obtained in any convenient manner. The esters can be obtained by suitable esterification of stilbenedicarboxylic acids. These acids are easily obtained by well known prior art methods, for example, as outlined in U.S. Pat. Nos. 2,677,703 and 2,688,631 and in the *Journal of the American Chemical Society*, 75, 2263 (1953).

The stilbenedicarboxylic acid compounds can be any of the ester-forming derivatives of stilbenedicarboxylic acid as well as the acid. Different isomers of stilbenedicarboxylic acid can be used such as the ortho-ortho', meta-meta', para-para', ortho-meta', ortho-para' etc. But the para-para' isomers hereinafter referred to as the "pp' stilbenedicarboxylic acid compounds " are preferred. Suitable ester-forming derivatives, as for example the esters, half-esters, acid chlorides etc., can be used. They can be aliphatic, cycloaliphatic, aromatic, or alkylaromatic esters of the stilbene oxirane dicarboxylic acids, for instance, alkyl esters such as methyl, ethyl, propyl, butyl, amyl, hexyl, heptyl and octyl stilbene dicarboxylates or cycloaliphatic, aryl and alkaryl esters derived from cyclopropyl carbinol, cyclobutanol, cyclopentanol, cyclohexanol, phenol, cresols, benzyl alcohol, and the like. The diethyl ester of p,p' stilbene oxirane dicarboxylic acid is generally utilized as it is readily prepared and possesses most of the desirable physical characteristics.

The glycols or their mixtures or two or more that are reacted with the stilbene oxirane dicarboxylic acid compound according to this invention can be any of the polyoxyalkylene glycols known to the art having alkylene radicals of from about 2 to 6 carbon atoms and containing from about 2 to 5 recurring oxyalkylene units. Examples of suitable polyoxyalkylene glycols are diethylene glycol, triethylene glycol, tetraethylene glycol, pentaethylene glycol, 1,6-hexanediol, the dimer, trimer etc. of 1,3-propylene glycol, or of 1,4-butylene glycol, etc. For this invention diols such as diethylene glycol, triethylene glycol and 1-6 hexanediol are generally preferred for their availability and for the desirable physical characteristics of the products derived from them.

Dibasic acid compounds other than the stilbenedicarboxylic acid compounds that can be mixed with the stilbenedicarboxylic acid compounds in this invention can be any of the organic acids characterized by the presence of two carboxyl groups. They can be aliphatic, unsaturated aliphatic, cycloaliphatic, or aromatic. Illustrative of suitable aliphatic acids are succinic acid, adipic acid, suberic acid etc. Unsaturated aliphatic acids which can be used are fumaric acid, maleic acid etc. Cycloaliphatic dicarboxylic acid such as cyclopentanedicarboxylic acid, cyclohexanedicarboxylic acid etc. are also suitable. Dicarboxylic aromatic acids which are suitable are illustrated by terephthalic acid and bibenzyl dicarboxylic acid, with terephthalic acid being preferred in this invention.

The broad class of polyester fiber-forming linear polymers from stilbene oxirane dicarboxylic acid and polyoxyalkylene glycols according to this invention, briefly stated, are prepared by heating a mixture comprising the stilbene oxirane dicarboxylic acid compound with an excess of the particular polyoxyalkylene glycol. The general reaction is usually carried out at atmospheric pressure, although subatmospheric or superatmospheric pressures may be utilized when such conditions appear desirable because of unusual physical characteristics of the reactants such as extremely low boiling points. Agitation is obtained conveniently by bubbling a stream of nitrogen or other inert gas slowly through the reaction mixture, although other means such as mechanical stirrers etc. also are suitable. Inert atmospheres are preferred. The reaction ordinarily requires a period of from about 5 to 20 hours at temperatures of from about 200° C. to 350° C. and preferably from 280° C. to 300° C. Other temperatures and heating periods sufficient to produce a linear polymer, the filaments of which are suitable for cold drawing, will depend on the particular reactants used and can be determined readily through common testing procedures.

More particularly, the fiber-forming linear polyesters of our invention are prepared suitably by heating dimethyl or diethyl stilbene oxirane dicarboxylic acid ester, and another dibasic acid ethyl or methyl ester if a mixed acid-type of linear polymer is desired, with an excess of the polyoxyalkylene glycol to be used. A small amount of an ester interchange catalyst, for example, 0.025 to 1% based on the total ester, may be added if desired and the mixture then heated at atmospheric pressure with gentle nitrogen bubbling until the methanol or ethanol used in esterifying the stilbene oxirane dicarboxylic acid and the other dibasic acid is present is evolved from the reaction mixture along with some of the excess unreacted polyoxyalkylene glycol if it is sufficiently low boiling. A vacuum may then be applied and the remainder of the excess polyoxyalkylene glycol drawn off. This process ordinarily requires from about 6 to 16 hours and usually is carried out at a temperature of about 280°–300° C. The product may then be heated further if necessary to melt it. Filaments are formed by extruding under pressure.

Two distinct reactions are involved in the above process of polymerization. The first reaction is the esterification or ester interchange of the stilbene oxirane dicarboxylic acid or its diester with the polyoxyalkylene glycol and the resultant formation of the corresponding glycol ester. The second reaction involves the formation of the linear polyester from the simple polyoxyalkylene glycol esters of stilbene oxirane dicarboxylic acid and is continued until a reaction product is obtained from which filaments can be formed that are suitable for cold drawing. The polyoxyalkylene glycol used in the formation of these linear polyesters ordinarily is present in an excess, with as high as 10–20 moles of glycol per mole of stilbene oxirane dicarboxylic acid compound being used preferably. Esterifying catalysts such as hydrogen chloride or para-toluene sulfonic acid can be used to speed up the esterification reaction if stilbene oxirane dicarboxylic acid or any of the other dibasic acids disclosed for the production of mixed acid polyesters per se are used in the reaction. The ester interchange reaction also can be promoted advantageously by the use of ester interchange catalysts such as lithium, sodium, magnesium etc. in the form of powder, chips, shavings, and the like.

When mixed acid polyesters are prepared according to this invention the stilbene oxirane dicarboxylic acid compound and the other polybasic acid compound reacted with the polyoxyalkylene glycol can be used in any desired proportions. Quantities as low as 1 weight percent of the stilbene oxirane dicarboxylic acid compound up to 100% of the acid compounds used can be used in the mixed acid polyesters to modify the melting point characteristic of the other dibasic acid polyesters. The particular proportions necessary to raise or lower the melting points of the products to any desired point are determined easily by workers in the art using known methods of testing.

Accordingly, the invention relates to compositions comprising 2,3-di-(carboxyphenyl) oxirane and polyalkylene 2,3-oxirane-di-(phenylcarboxylate) linear polymers therefrom. The 2,3-di-(carboxyphenyl) oxiranes of this invention comprise 2,3-di-(4-carboxyphenyl) oxirane; 2,3-di-(3-carboxyphenyl) oxirane; 2-(3-carboxyphenyl)-3-(4-carboxyphenyl) oxirane; 2,3-di-(2-carboxyphenyl) oxirane; 2-(2-carboxyphenyl)-3-(4-carboxyphenyl) oxirane; and 2-(2-carboxyphenyl)-3-(3-carboxyphenyl) oxirane. The linear polymers comprise polyalkylene oxirane-2,3-di(4-phenylcarboxylates) wherein the alkylene group has from 2 to 24 carbon atoms and comprise polyethylene oxirane-2,3-di(4-phenylcarboxylate); poly-1,4-butylene oxirane-2,3-di(4-phenylcarboxylate); poly-1,6-hexylene oxirane-2,3-di(4-phenylcarboxylate); poly-1,22-docosenyl oxirane-2,3-di(4-phenylcarboxylate) and poly-1,24-tetracosenyl oxirane-2,3-di(4-phenylcarboxylate).

This invention also relates to essentially linear copolyesters comprising units of a dihydric alcohol or alcohols moiety and a dicarboxylate component comprising aliphatic or aromatic dicarboxylate moieties and 2,3-dicarboxyphenyl oxirane moieties in mole ratios such that the units of the dihydric alcohol or alcohols moiety to the dicarboxylate moiety are in the ratio of from 1:19 to 19:1.

The following examples serve to illustrate the preparation of 2,3-dicarboxyphenyl oxirane and polyalkylene oxirane-2,3-diphenylcarboxylate linear polymers in accordance with our invention. These examples are to be regarded solely as illustrative and not as restricting the scope of the invention.

EXAMPLE I

Into a 250 ml 3-neck flask equipped with thermometer, stirring bar, pressure-equalizing funnel, condenser, and $N_2$ bubbler was placed 3.24 g (0.01 m) of 4,4'-dicarboethoxystilbene, 75 ml of $CH_2Cl_2$ and 11.7 g (0.11 m) of sodium carbonate. The reactor was cooled to 15° C. and to it was added a prepared solution of 1 ml of 90% $H_2O_2$ in 9.3 ml of trifluoroacetic acid dissolved in 10 ml of $CH_2Cl_2$. The reaction exothermed to 30° C. and then was refluxed at 38° C. for 30 minutes. Solids were filtered and the $CH_2Cl_2$ removed on a Rotovap evaporator to yield 3.2 g (97% yield) of diethylester of 2,3-di-(4-carboxyphenyl) oxirane (DCO) melting at 109°–111° C.

EXAMPLE II

Preparation of the polyester with 1,6-hexanediol was as follows:

A mixture of 5.0 g of DCO and 3.07 g of 1,6-hexanediol was placed in a test tube equipped with nitrogen bubbler and side arm. Full melt was obtained upon heating to 180° C., then 0.05 ml of tetrabutyltitanate was added. The viscous mixture was heated at 200° C. for 2.0 hours with a nitrogen blanket. The temperature was raised to 268° C. and simultaneously vacuum was applied over a 17 minute period. Full vacuum (0.26 mm Hg) was continued for 129 minutes. The product (poly-1,6-hexylene oxirane-2,3-di(4-phenylcarboxylate)) was semi-transparent and had an amber color. Infrared absorption characteristics of the epoxide were observed for the polymer at 1265 cm$^{-1}$ (m), 850 cm$^{-1}$ (m), and 765 cm$^{-1}$ (m). The glass transition temperature (Tg) of the polymer was 116° C., and the polyester was amorphous. Thermal analysis (TGS) showed no loss of weight up to 290° C. and 1% loss at 345° C.

EXAMPLE III

A mixture of 5.0 g of DCO and 1.67 g of ethylene glycol is reacted according to the procedure of Example II to prepare polyethylene oxirane-2,3-di(4-phenylcarboxylate). The glass transition temperature (Tg) is calculated to be 203° C.

EXAMPLE IV

A mixture of 5.0 g of DCO and 2.43 g of 1,4-butanediol is reacted according to the procedure of Example II to prepare poly-1,4-butene oxirane-2,3-di(4-phenylcarboxylate). The glass transition temperature (Tg) is calculated to be 137° C.

What is claimed is:

1. A 2,3-di-(carboxyphenyl) oxirane compound of the structural formula

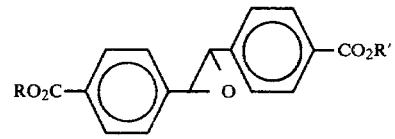

wherein R and R' are individually selected from the group consisting of hydrogen, alkyl, aryl and alkaryl moieties wherein the alkyl moieties contain from 1 to 24 carbon atoms and the aryl moieties contain from 6 to 24 carbon atoms.

2. The compound of claim 1 wherein the said 2,3-di-(carboxyphenyl) oxirane compound is a diacid.

3. The compound of claim 1 which is 2,3-di-(4-carboxyphenyl) oxirane.

4. The compound of claim 1 which is 2,3-di-(3-carboxyphenyl) oxirane.

5. The compound of claim 1 which is 2-(3-carboxyphenyl)-3-(4-carboxyphenyl) oxirane.

6. The compound of claim 1 which is 2,3-di-(2-carboxyphenyl) oxirane.

7. The compound of claim 1 which is 2-(2-carboxyphenyl)-3-(4-carboxyphenyl) oxirane.

8. The compound of claim 1 which is 2-(2-carboxyphenyl)-3-(3-carboxyphenyl) oxirane.

9. The compound of claim 1 wherein the said 2,3-dicarboxyphenyl oxirane compound is a diester of a monohydroxy compound containing 1 to 24 carbon atoms.

10. The compound of claim 9 wherein the said diester is the dimethylester of 2,3-di-(4-carboxyphenyl) oxirane.

11. The compound of claim 9 wherein the said diester is the diethyl ester of 2,3-di-(4-carboxyphenyl) oxirane.

12. The compound of claim 9 wherein the said diester is the di-n-butyl ester of 2,3-di-4(-carboxyphenyl) oxirane.

13. A resinous polymer comprising recurring units of an acyl compound wherein said acyl compound comprises a polyacyl radical of a 2,3-di-(carboxyphenyl) oxirane of the structural formula

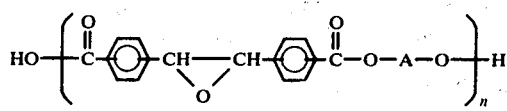

wherein n comprises a whole number from 1 to 8000 inclusive, A is selected from the group consisting of divalent aliphatic moieties, divalent arene moieties and divalent cycloalkyl moieties.

14. The polymer of claim 13 wherein the said divalent aliphatic moiety comprises an alkylene group having 2 to 24 carbon atoms in the alkylene chain.

15. The polymer of claim 13 wherein said divalent cycloalkyl moiety is a dimethylcyclohexyl moiety.

16. The polymer of claim 13 wherein the said acyl compound comprises 2,3-di-(4-dicarboxyphenyl) oxirane.

17. The polymer of claim 16 wherein A comprises ethylene.

18. The polymer of claim 16 wherein A comprises 1,4-butylene.

19. The polymer of claim 13 which is polyethylene-2,3-oxirane-di(4-phenylcarboxylate).

20. The polymer of claim 13 which is poly-1,4-butylene-2,3-oxirane-di-(4-phenylcarboxylate).

21. The polymer of claim 13 which is poly-1,6-hexylene-2,3-oxirane-di-(4-phenylcarboxylate).

22. The polymer of claim 13 which is poly-1,24-tetracosenyl oxirane-2,3-di-(4-phenylcarboxylate).

23. The polymer of claim 13 wherein the acyl moieties of said polyacyl radical of a 2,3-di-(carboxyphenyl) oxirane comprise at least 1 weight percent of the acyl moieties in the said acyl compound.

24. The polymer of claim 23 wherein the acyl moeties of the said acyl compound comprise acyl moieties of a 2,3-di-(carboxyphenyl) oxirane and polycarboxy compounds selected from the group consisting of terephthalic acid, phthalic acid, phthalic anhydride, isophthalic acid, 2,6-naphthalene dicarboxylic acid, trimellitic acid, trimellitic anhydride, adipic acid, sebacic acid, 1,2,3,4-butane-tetracarboxylic acid, maleic acid, maleic anhydride, fumaric acid and mixtures thereof.

* * * * *

UNITED STATES PATENT OFFICE
CERTIFICATE OF CORRECTION

Patent No. 4,248,998          Dated February 3, 1981

Inventor(s) Carl A. Udovich, Edward E. Paschke and Ellis K. Fields

It is certified that error appears in the above-identified patent and that said Letters Patent are hereby corrected as shown below:

| Patent Column | Line | |
|---|---|---|
| 7 | 48 | "polydric" should read --polyhydric-- |
| 9 | 7 | "115-125 should be placed in correct column under $T_g\ ^\circ C$ |
| 9 | 14 | "advantages" should read --advantage-- |
| 9 | 29 | "used" should read --use-- |
| 11 | 50 | "or two" should read --of two-- |

Signed and Sealed this

Twenty-first Day of July 1981

[SEAL]

Attest:

Attesting Officer

GERALD J. MOSSINGHOFF

Commissioner of Patents and Trademarks